United States Patent
Moehrle

(10) Patent No.: US 10,571,389 B2
(45) Date of Patent: Feb. 25, 2020

(54) DIRECT EXAMINATION OF BIOLOGICAL MATERIAL EX VIVO

(71) Applicant: Eberhard-Karls-Universitaet Tuebingen Universitaetsklinikum, Tuebingen (DE)

(72) Inventor: Matthias Moehrle, Tuebingen (DE)

(73) Assignee: Eberhard-Karls-Universitaet Tuebingen Universitaetsklinikum, Tuebingen (DE)

( * ) Notice: Subject to any disclaimer, the term of this patent is extended or adjusted under 35 U.S.C. 154(b) by 458 days.

(21) Appl. No.: 13/678,998

(22) Filed: Nov. 16, 2012

(65) Prior Publication Data
US 2013/0078648 A1 Mar. 28, 2013

Related U.S. Application Data

(63) Continuation of application No. PCT/EP2011/055730, filed on Apr. 12, 2011.

(30) Foreign Application Priority Data

May 19, 2010 (DE) .................. 10 2010 021 534

(51) Int. Cl.
| | | |
|---|---|---|
| *G01N 21/17* | (2006.01) | |
| *G01N 1/30* | (2006.01) | |
| *G01N 21/21* | (2006.01) | |
| *G02B 21/33* | (2006.01) | |
| *A61B 5/00* | (2006.01) | |
| *G02B 21/34* | (2006.01) | |

(52) U.S. Cl.
CPC .......... *G01N 21/17* (2013.01); *A61B 5/0059* (2013.01); *A61B 5/444* (2013.01); *G01N 1/30* (2013.01); *G01N 21/21* (2013.01); *G02B 21/33* (2013.01); *G02B 21/34* (2013.01)

(58) Field of Classification Search
CPC . A61B 5/0059; A61B 1/00186; A61B 1/0646; A61B 5/14556; A61B 5/444; A61B 1/043; G02B 21/082; G01N 1/30; G01N 21/21
USPC ........................................................ 435/7.21
See application file for complete search history.

(56) References Cited

U.S. PATENT DOCUMENTS

| 3,629,577 A | 12/1971 | Karlsruhe et al. ........... 250/49.5 |
| 4,425,507 A | 1/1984 | Panov et al. ................ 250/442.1 |
| 4,627,009 A | 12/1986 | Holmes et al. ............... 364/559 |

(Continued)

FOREIGN PATENT DOCUMENTS

| CH | 514 840 | 12/1971 | ............ G01N 23/04 |
| DE | 579 789 | 6/1933 | |

(Continued)

OTHER PUBLICATIONS

Williams et al., PNA Fluorescent in Situ Hybridization for Rapid Microbiology and Cytogenetic Analysis, Peptide Nucleic Acids, vol. 208, 2002, pp. 181-193.*
Steven L. Jacques, Jessica C. Ramella-Roman, and Ken Lee, "Imaging skin pathology with polarized light, "Journal of Biomedical Optics 7(3), 329-340, Jul. 2002.*

(Continued)

*Primary Examiner* — Erik B Crawford
(74) *Attorney, Agent, or Firm* — Harness, Dickey and Pierce, P.L.C.

(57) ABSTRACT

The present invention relates to a method for the visual examination of biological material ex vivo and an apparatus for the sterical orientation of biological material which can be used in said method.

10 Claims, 8 Drawing Sheets

(56) References Cited

U.S. PATENT DOCUMENTS

| | | | |
|---|---|---|---|
| 6,671,540 B1* | 12/2003 | Hochman | A61B 5/0059 600/431 |
| 7,372,985 B2* | 5/2008 | So et al. | 382/133 |
| 2001/0056237 A1* | 12/2001 | Cane | A61B 5/0059 600/475 |
| 2002/0007123 A1 | 1/2002 | Balas | 600/476 |
| 2003/0026762 A1* | 2/2003 | Malmros et al. | 424/9.6 |
| 2004/0111031 A1* | 6/2004 | Alfano | A61B 5/0059 600/476 |
| 2004/0174525 A1* | 9/2004 | Mullani | A61B 5/0059 356/369 |
| 2004/0249274 A1 | 12/2004 | Yaroslavsky et al. | 600/431 |
| 2012/0029348 A1* | 2/2012 | Yaroslaysky et al. | 600/431 |

FOREIGN PATENT DOCUMENTS

| | | | |
|---|---|---|---|
| EP | 0025122 | 3/1981 | G02B 21/26 |
| WO | WO 93/25141 | 12/1993 | A61B 5/00 |
| WO | WO 01/08552 | 2/2001 | A61B 5/00 |
| WO | WO 03/091729 | 11/2003 | G01N 33/50 |

OTHER PUBLICATIONS

Vanessa Campo-Ruiz, Dinesh Patel, R.Rox Anderson, Emilio Delgado-Baeza and Salvador Gonzalez, "Evaluation of human knee meniscus biopsies with near-infrared reflectance confocal microscopy, A pilot study", Int. J. Exp. Path. 2005, 86, 297-307.*

"Microscope." Merriam-Webster.com. Merriam-Webster, n.d. Web. May 1, 2017.*

Ramella-Roman, J., et al. (2008) "Out of plane polarmetric imaging of skin: surface and subsurface effects" Proceedings of the Nato Advanced Study Institute on Optical Waveguide Sensing and Imaging in Medicine, Environment, Security and Defence Springer Netherlands, pp. 259-269.

Salomatina, E., et al. (2009) "Multimodal optical imaging and spectroscopy for the intraoperative mapping of nonmelanoma skin cancer" Journal of Applied Physics, 105(19):102010-1-102010-7.

Yu, L., et al. (2009) "Caveats in BerEP4 staining to differentiate basal and squamous cell carcinoma" Journal of Cutaneous Pathology, 36(10):1074-1076.

International Search Report for PCT/EP2011/055730 dated Sep. 27, 2011.

International Preliminary Report on Patentability for PCT/EP2011/055730 dated Nov. 20, 2012.

* cited by examiner

DIRECT EXAMINATION OF BIOLOGICAL MATERIAL EX VIVO

CROSS-REFERENCE TO RELATED APPLICATIONS

This application is a continuation of copending international patent application PCT/EP2011/055730 filed on 12 Apr. 2011 and designating the U.S., which has been published in German, and claims priority from German patent application DE 10 2010 021 534.1 filed on 19 May 2010. The entire contents of these prior applications are incorporated herein by reference.

FIELD

The present invention pertains to methods for the visual examination of biological material ex vivo and an apparatus for the sterical orientation of biological material applicable in this method.

BACKGROUND

The visual examination of biological material plays a central role in the detection of pathological alterations. In the field of dermato-surgery it is e.g. routinely tested whether the cutting margins of tissue material which has been surgically removed are located in sano, i.e. in the healthy tissue, to make sure that the tumor material has been completely removed. It has been demonstrated that this histological control of the three-dimensional margins of excisions, which is also referred to as three-dimensional histology, reduces the risk of local recurrences and is, therefore, the method of first choice for many tumors of the skin.

So far, the visual examination of the cutting margins within the context of the three-dimensional histology is realized at tissue sections which were previously prepared from the removed biological material.

In the USA and in parts also in Europe the control of the cutting margins is made with frozen or quick sections. This method is also referred to as "Mohs' Surgery" according to its originator Frederic E. Mohs. In this method the removed biological material is deep frozen. Out of this frozen tissue sections of a thickness of about 5 to 10 µm are prepared. The sections are then visually examined by transmission microscopy. The results of this examination are available within 30 to 45 minutes. However the frozen or quick section methods are imprecise and can only be used in a reliable manner for solid, nodular basal cell carcinomas.

More precise results can be obtained by the so-called paraffin section method. In this method the removed biological material is embedded into paraffin. Then tissue sections are prepared and again examined by transmission microscopy. However, because of the complex sample preparation the results of the examination are only available about 20 hours after the removal of the biological material. For this reason it is e.g. not possible, in case of the detection of branches of a tumor at the cutting margin, to make a subsequent excision in a targeted manner within the same surgery. As a consequence, the cutting areas or wounds are often kept open until the result is available which means a high stress and high risk of infection for the patient.

Another decisive disadvantage of the before-mentioned section methods is the fact that the examined biological material is so to say "consumed" and no longer available for e.g. histological or molecular biological examinations and other processes. If such further examinations would be necessary biological material is again to be taken from the affected patient which could again require narcoses and other surgical risks.

The confocal laser scanning microscopy is a method where so-called optical sections are prepared allowing a histopathological assessment of biological material. The depth of penetration is about 0.3 mm allowing the evaluation of the tumor excision from the cutting margin from the outside. However the confocal laser scanning microscopy is technically complex and the diagnostic reliability is insufficient.

SUMMARY

Against this background the problem underlying the present invention is to provide methods for the visual examination of biological material ex vivo wherein the disadvantages of the currently used methods are avoided. In particular such a method should be provided which makes examination results available within a short time and where the removed biological material is not consumed.

This problem is solved by a method for the visual examination of biological material ex vivo comprising the following steps: 1. Providing biological material, 2. labeling the biological material, 3. switching off of reflections at the surface of the biological material, and 4. examining the biological material by reflected light microscopy, wherein the provided biological material is vital biological material which is neither histologically nor optically cut.

The problem underlying the invention is completely solved by this method.

DETAILED DESCRIPTION

Figure 1A:
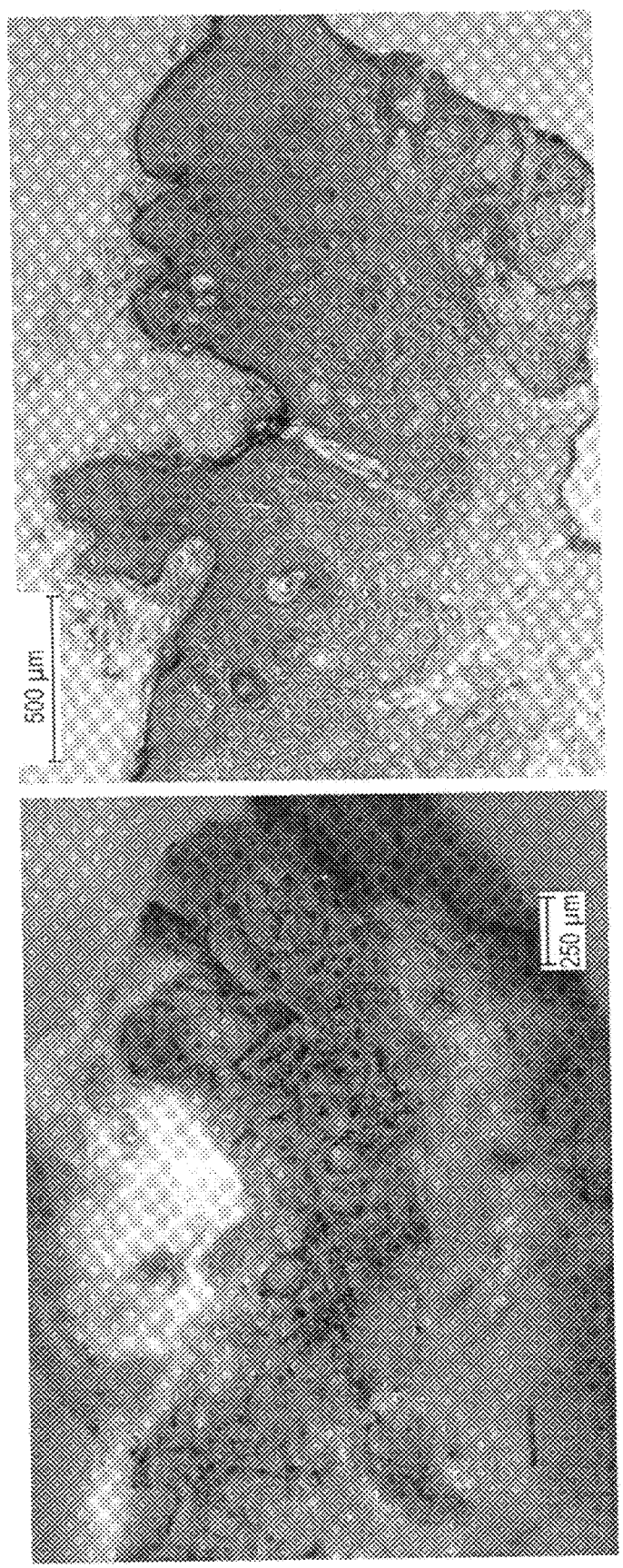
FIG. 1 shows a comparison of the examination results obtained by means of the method according to the invention (left) and by means of the classical paraffin section method after HE staining (right) exemplified with the squamous cell carcinoma (A, B), the solid basal cell carcinoma (C) and the mixed basal cell carcinoma ("mixed type") (D)
Figure 1B:
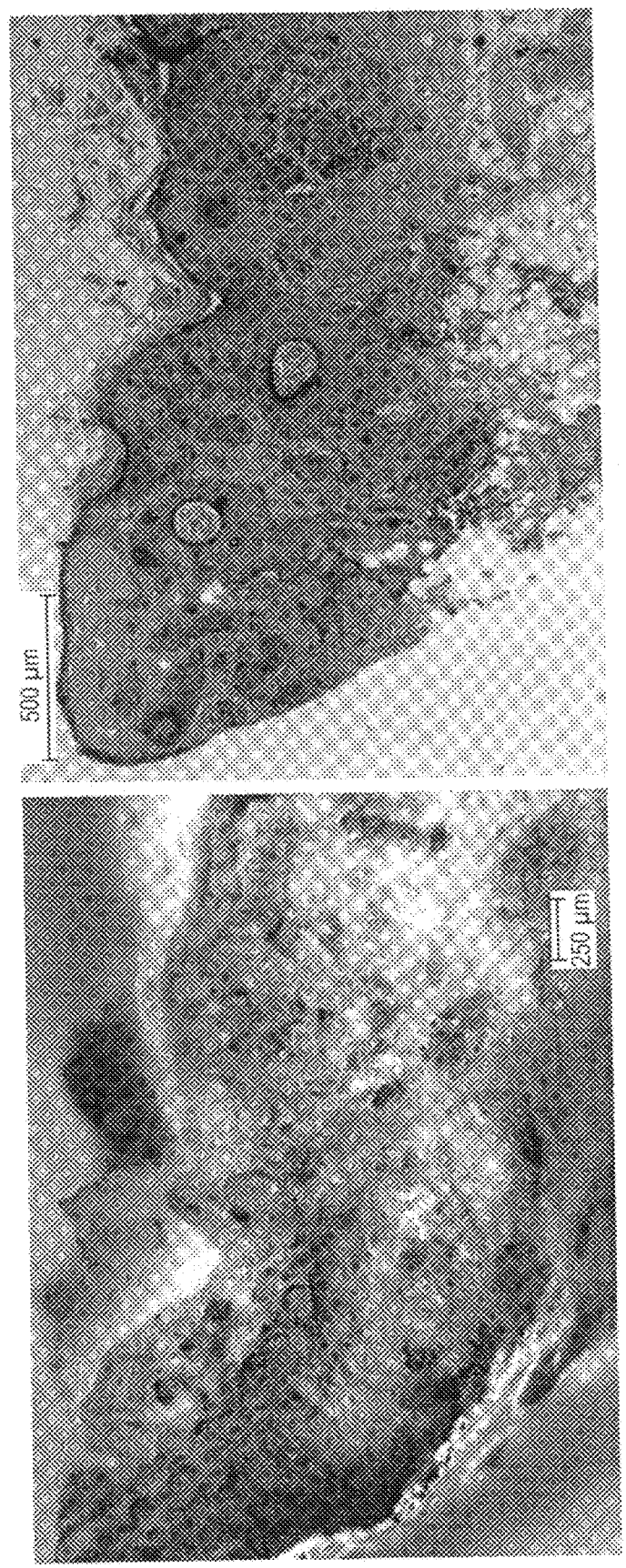
Figure 1C:
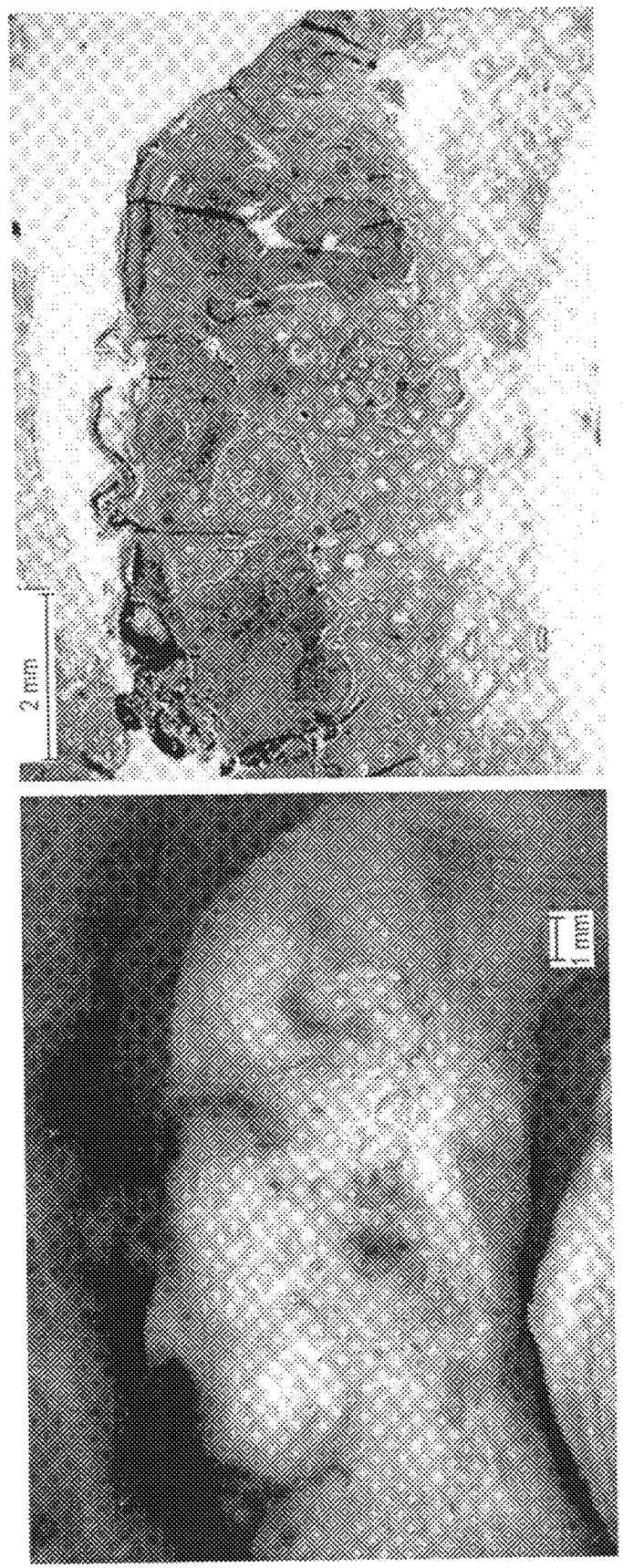
Figure 1D:
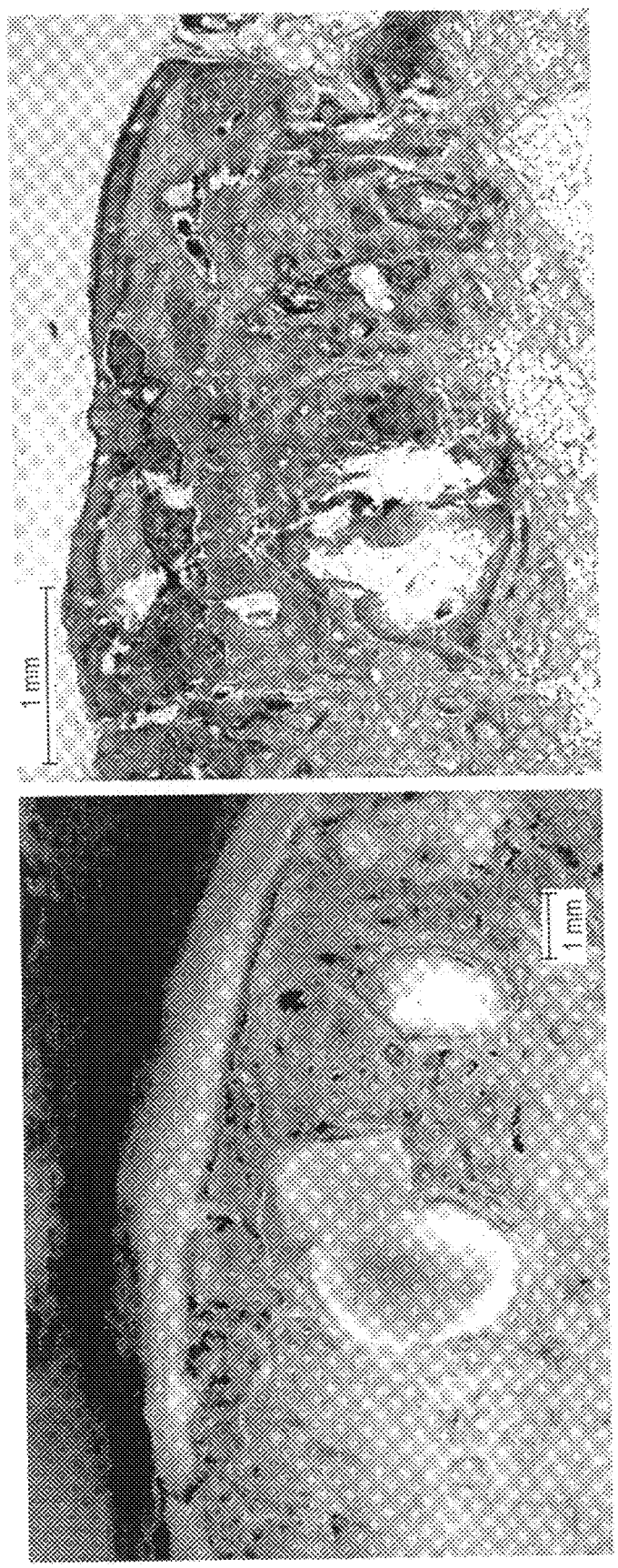

Any biological material may be used in the methods according to the invention for examination ex vivo, such as tissue from any organ. Examples of important organs are the skin, connective tissue, nervous tissue, viscera, muscle, blood vessels etc.

The methods according to the invention are particularly suited for the cutting margin control in dermato-surgery.

The methods according to the invention have the particular advantage that in the run-up to an examination the removed biological material need not to be histologically or optically cut.

As used herein, "histological cutting" refers to the preparation of sections at or of biological material, respectively, by means of a cutting device, such as a knife or a microtome, with section thicknesses of usually 5 to 10 µm or 20 µm, respectively.

As used herein, "optical cutting" refers to the complex preparation of optical sections by means of confocal microscopy, such as the confocal laser scanning microscopy or the confocal fluorescence microscopy.

According to the invention, a complex sample preparation or treatment for the purpose of a histological cutting or the preparation of optical sections is not necessary. Rather, the methods according to the invention provide results within a few minutes after the provision of the biological material. Thereby, the methods according to the invention do not only provide results significantly faster than the paraffin section method and the confocal laser scanning microscopy but also faster than the frozen or quick section method ("Mohs' Surgery"). Furthermore, the methods of the invention also provide more accurate results than the Mohs' Surgery or also the confocal laser scanning microscopy method. For this reason it is, e.g., possible within the context of the cutting margin control to immediately recut within the same surgery session in case the initial cut was not located in sano.

Furthermore the biological material is not consumed by a sample preparation, freezing or embedding and will be available for further examinations or treatments. The biological material provided according to the invention is still "vital" since it is freshly removed and still has metabolic activity.

The thickness of the biological material as provided according to the invention is above that of a thin section, therefore it is >10 μm, preferably >20 μm, preferably >50 μm, further preferably >100 μm. The biological material provided according to the invention is, e.g., tissue of the skin removed by means of a surgical excision, and has thicknesses of approx. 0.2 mm to approx. 30 mm.

According to the invention the examination by reflected light microscopy is performed by means of a stereo microscope or a digital microscope.

As used herein "labeling" of the biological material refers to a treatment of the biological material in such a manner that it can be visually examined in an improved manner, for example, a staining by means of histological dyes or immunostaining.

Since the provided biological material is usually freshly removed it comprises moisture. At the interface between the moist biological material and the air surface light reflections might occur which makes an examination by reflected light microscopy difficult. According to the invention such reflections at the surface of the biological material are switched off by means known to the skilled person.

As the inventors have been able to demonstrate in a trial with a plurality of preparations from patients with a clinical suspicion of basal cell carcinomas, the methods according to the invention provide diagnostically reliable results. An excellent correlation between the methods according to the invention and the paraffin section method of the prior art could be shown.

In another embodiment of the method according to the invention step 1 comprises the following step: 1.1 moisturizing the biological material.

This measure has the advantage that the provided biological material, if it is insufficiently moist or even dry, can be reliably visually examined. To moisturize, the common solutions can be used which are appropriate for this purpose, such as water, saline, biological buffer, etc.

In another embodiment step 1.1 of the method according to the invention comprises the following step: 1.1.1 fixing the biological material.

This measure has the advantage that an even better visual examination of the biological material is enabled. The fixing is realized with common fixation solutions, such as 10% acetic acid or 4.5% formalin. Preferably the fixation is made at minimum, i.e. only within a few seconds, <1, 2, 3 or preferably <10 seconds. In doing so, the biological material is not "consumed", but is available for further examinations or treatments without any restrictions. As the inventors were able to demonstrate by such a minimum fixation, the quality of subsequently prepared classical paraffin sections remains unchanged.

In another embodiment of the method according to the invention the switching off of reflections at the biological material is realized/performed by the use of a transparent medium and a glass carrier, wherein the transparent medium is essentially deposited without the inclusion of air or gas between the biological material and the glass carrier and is brought into direct contact with the latter.

This measure has the advantage that reflections at the surface of the biological material are switched off by a simple and effective way. The transparent medium can be a liquid, such as water or saline, or a gel, such as ultrasonic gel. A suitable glass carrier is for example a commercially available object slide or a cover slip for microscopy.

In another embodiment of the method according to the invention the switching off of reflections at the biological material is realized by the use of polarized light in the examination by reflected light microscopy (polarization microscopy).

This method has the advantage that it is refrained from the use of a glass carrier which might complicate the three-dimensional inspection of the biological sample. The use of polarized light can e.g. be realized by a polarization microscope comprising two polarization filters. The first polarization filter, also referred to as polarizer or primary filter, linearly polarizes the light of the light source of the microscope, i.e. only light swinging in a first polarization plane can pass. A second polarization filter referred to as analyzer or secondary filter, is rotated with respect to the first filter by 90°. The direction of oscillation of the previously linearly polarized light is then oriented in such a way that it is completely blocked by the analyzer. Thereby, reflections at the biological material in the reflected light microscopic examination are abolished.

In another embodiment of the method according to the invention the labeling of the biological material comprises a staining reaction at the latter.

This method has the advantage that the contrast in the biological material is increased and the visual examination is thereby facilitated. The staining reaction can be a quick staining with typical histological dyes such as haemalum, toluidine blue, haematoxylin, picrofuchsin, eosin, etc. The inventors also realized that a staining reaction does not affect the biological tissue which is still available for further examinations.

In another embodiment of the method according to the invention the labeling of the biological material comprises a specific immunoreaction with the latter, which preferably comprises the following steps: 2.1 contacting the biological material with a primary antibody for binding the latter to the biological material, 2.2 removing the primary antibody which has not bound from the biological material, and 2.3 detecting a specific binding of the primary antibody to the biological material, which preferably comprises the following further steps: 2.3.1 contacting the biological material with a secondary antibody to bind the latter to the primary antibody, and 2.3.2 detecting a specific binding of the secondary antibody to the primary antibody.

This measure has the advantage that through the use of highly specific and selective antibodies the provided biological material can be examined within a few minutes, where applicable still in the operating room, for the presence of specific structures such as tumor markers. By doing so a diagnostic examination is again improved. According to the findings of the inventors also this specific immunostaining does not consume the biological material.

Another subject matter of the present invention is an apparatus for the sterical orientation of biological material which can be used to perform the method according to the invention, and which comprises the following:

- a receiving element to receive a carrier for the biological material,
- a holding element which is rotably connected to the receiving element, and
- a base element which is rotably connected to the holding element.

The apparatus according to the invention enables in a preferred way the inspection of the provided biological material, which is located on the carrier, from all sides, i.e. spatially or three-dimensionally, respectively. In doing so, e.g., skin excisions can be examined with respect to their cutting margins in accordance with the three-dimensional histology.

As used herein, "rotably connected" means that the respective elements can be rotated relatively to each other by up to 360°, i.e. completely or unlimited, respectively.

The carrier for the biological material can be a glass carrier such as a classical object slide.

According to the invention it is preferred if the receiving element comprises a fastening element, preferably a vacuum cup, to fasten the carrier for the biological material.

The method has the advantage that, for example, a commercially obtainable microscope slide can be fastened to the receiving element and can be removed from the latter in a simple fashion.

It is further preferred if the holding element of the apparatus according to the invention is connected with the receiving element via a first rotary axis in a rotable manner, and/or the base element is connected with the holding element via a second rotary axis in a rotable manner.

These measures have the advantage that a rotating joint is realized between each of the elements in a simple way.

According to a preferred further development of the apparatus according to the invention the base element is connected with a foot element for positioning the apparatus on a horizontal plane, preferably via a third rotary axis in a rotable manner.

This measure has the advantage that the apparatus is easier to manage, and can, e.g., be positioned under the objective of the microscope on the working surface even in the operating room. Because of the rotatability, alternatively a rotation of the entire apparatus on a horizontal plane is avoided in order to three-dimensionally examine the biological material.

The method according to the invention is preferably configured for a use in a method for a visual examination of biological material ex vivo, which is preferably any of the above-described methods according to the invention.

It goes without saying that the before-mentioned features and those to be mentioned in the following can be used not only in the combination indicated in each case but also in other combinations or in isolated position without departing from the scope of the invention.

The present invention is now explained in more detail by means of embodiments which are of pure illustrative character and do not limit the scope of the invention. Reference is made to the enclosed figures

EXAMPLES

Example 1

Comparison of the Method According to the Invention and the Paraffin Section Method after HE Staining The method according to the invention was tested with several skin cancer preparations, namely a squamous cell carcinoma (SCC) and different forms of basal cell carcinomas (BCC). Tumor-free skin tissue served as a control. For this purpose, strips of tissues from so-called "loaf-of-bread" sections or from lateral resection margins and so-called "muffin" preparations were obtained.

For performing the method according to the invention the sample preparation was made according to the following protocol:

| | | |
|---|---|---|
| Fixing | 10% acedic acid ("glacial acedic acid", Merck, Darmstadt, Germany) | 40 sec |
| Rinsing | tap water | 10 sec |
| Staining | 0.2% toluidine blue (Merck, Darmstadt, Germany) | 40 sec |
| Rinsing | tap water | 5 sec |
| In total | | 95 sec |

In the following HE paraffin sections were prepared from all examined samples according to standard procedures.

The following table 1 shows the number of samples examined by a "classical" histological analysis by using the paraffin section method and using a haematoxylin and eosin staining (HE staining). A stereo microscope (Leica M205 FA) and a digital microscope (Keyence VHX-600K) were used. All of the 129 samples were examined with the digital microscope, 78 samples thereof were also examined with the stereo microscope. In the following all of the 129 samples were prepared with HE paraffin section method.

TABLE 1

| | Examined samples | | | | | |
|---|---|---|---|---|---|---|
| | Tissue strips | | "Muffins" | | Total | |
| HE staining (Paraffin sections) | Stereo microscope | Digital microscope | Stereo microscope | Digital microscope | Stereo microscope | Digital microscope |
| Tumor-free | 18 | 27 | 5 | 15 | 23 | 42 |
| Solid BCC | 32 | 57 | 2 | 5 | 34 | 62 |

TABLE 1-continued

| | Examined samples | | | | | |
|---|---|---|---|---|---|---|
| | Tissue strips | | "Muffins" | | Total | |
| HE staining (Paraffin sections) | Stereo microscope | Digital microscope | Stereo microscope | Digital microscope | Stereo microscope | Digital microscope |
| Fibrotic BCC | 3 | 5 | 0 | 0 | 3 | 5 |
| Superficial BCC | 10 | 10 | 0 | 1 | 10 | 11 |
| Mixed BCC | 1 | 1 | 0 | 0 | 1 | 1 |
| Squamous cell carcinoma (SCC) | 7 | 8 | 0 | 0 | 7 | 8 |
| Total | 71 | 108 | 7 | 21 | 78 | 129 |

The results which were obtained by means of the classical paraffin section method have been compared to those from the method according to the invention using a digital microscope and a stereo microscope with respect to sensitivity, specificity and the positive predictive value (PPV) and the negative predictive value (NPV). Samples showing a squamous cell carcinoma in the HE stained sections were excluded from the analysis.

The qualitative result of this comparison is shown in FIG. 1 and the quantitative result is shown in the following table 2:

TABLE 2

| | Digital microscopic examination | | | |
|---|---|---|---|---|
| | Sensitivity | Specificity | PPV | NPV |
| In total (n = 121) | 91% | 90% | 93% | 88% |
| Tissue strips (n = 100) | 92% | 89% | 86% | 94% |
| "Muffins" (n = 21) | 83% | 93% | 83% | 93% |

The above-mentioned comparison was made analogically by using a stereo microscope. The quantitative result of this comparison is shown in the following table 3:

TABLE 3

| | Stereo microscopic examination | | | |
|---|---|---|---|---|
| | Sensitivity | Specificity | PPV | NPV |
| In total (n = 71) | 95% | 94% | 95% | 94% |
| Tissue strips (n = 64) | 95% | 93% | 95% | 93% |
| "Muffins" (n = 7) | 100% | 100% | 100% | 100% |

It is shown in an impressive manner that the results of the examination with the method according to the invention highly correlate with the classic standard method (HE stained paraffin sections). Therefore, the method has a high precision and reliability. A microscopic existing tumor, e.g. a basal cell carcinoma, can be diagnosed by the method according to the invention with a very high accuracy. If a tumor cannot be detected by the method according to the invention the microscopic existence of a tumor can be excluded with high accuracy.

Example 2

Immunohistological Labeling in the Context of the Method According to the Invention Tissue samples were removed from patients with basal cell carcinomas and, within a context of the method according to the invention, subjected to an immunostaining with a monoclonal antibody directed against the epithelial specific antigen (ESA) or the epithelial cellular adhesion molecule (Ep-CAM) referred to as BerEp4. The protocol of the sample preparation was as follows.

| | | |
|---|---|---|
| Fixing | 4.5% formaline[1] | 30 sec |
| Rinsing | tap water | 10 sec |
| Blocking of endogenous peroxidase | $H_2O_2$ 3%[2] | 30 sec |
| Primary antibody | BerEp4 1:50[3] | 90 sec |
| Rinsing | TBS[4] | 10 sec |
| Secondary antibody | EnVision[5] | 90 sec |
| Rinsing | TBS[4] | 10 sec |
| Staining | DAB + Chromogen[6] | 90 sec |
| Rinsing | tap water | 10 sec |
| Rinsing | aqua dest | 3 sec |
| Counterstaining | haematoxylin[7] | 10 sec |
| Rinsing | aqua dest | 3 sec |
| Rinsing | tap water | 10 sec |
| In total | | approx. 7 min |

Figure 2A:
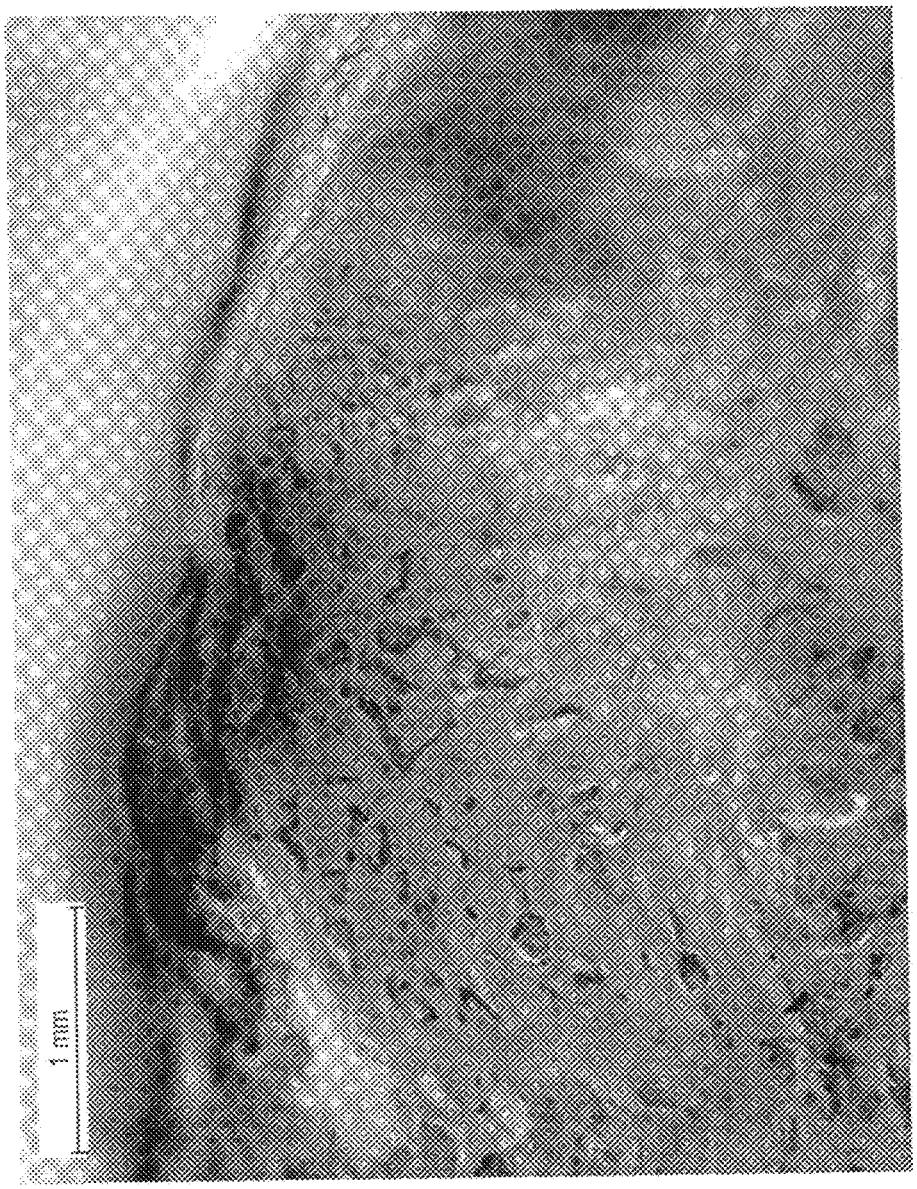
FIG. 2 shows the result of a immunohistological examination by means of the method according to the invention with fibrotic basal cell carcinomas at different levels of magnification (A to C) by use of an anti-BerEp4 antibody.
Figure 2B:
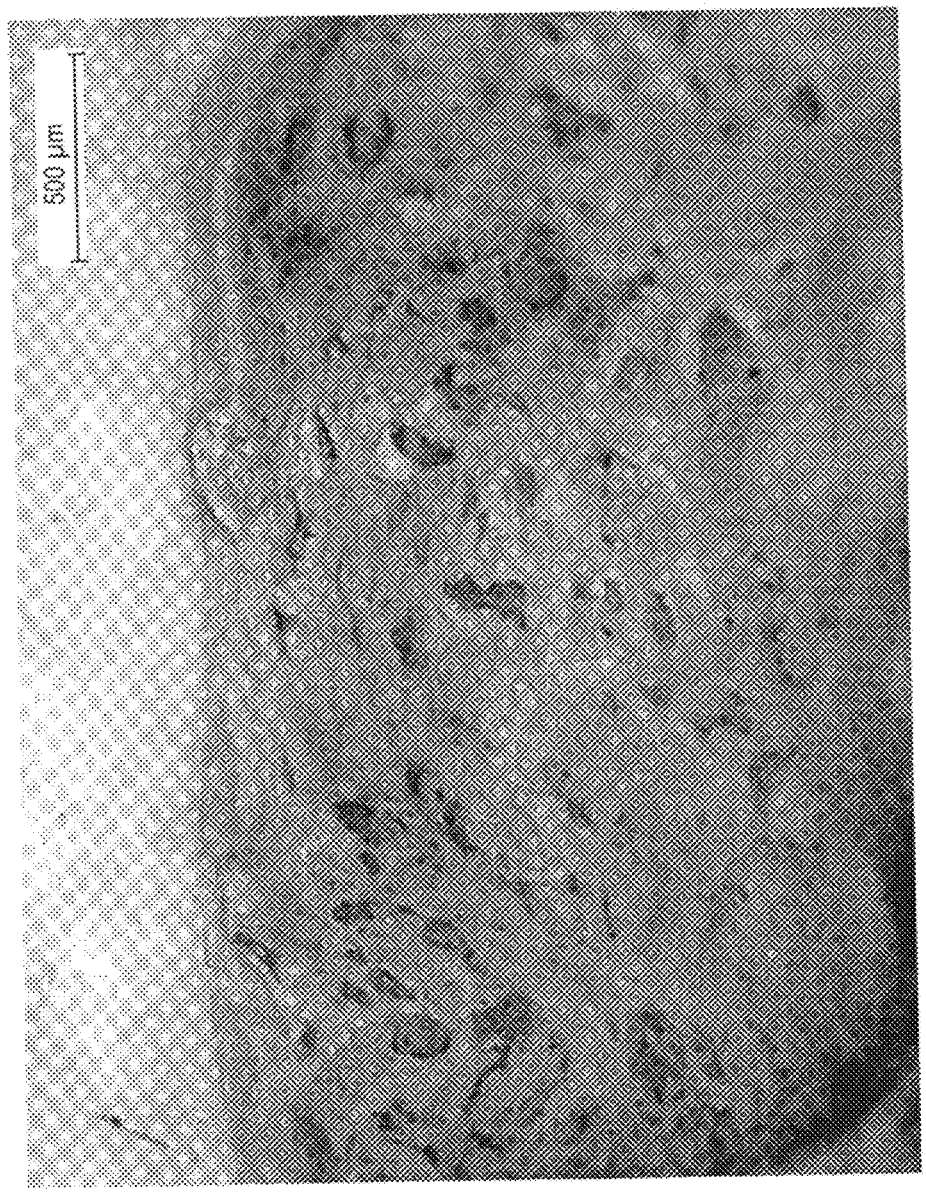
Figure 2C:
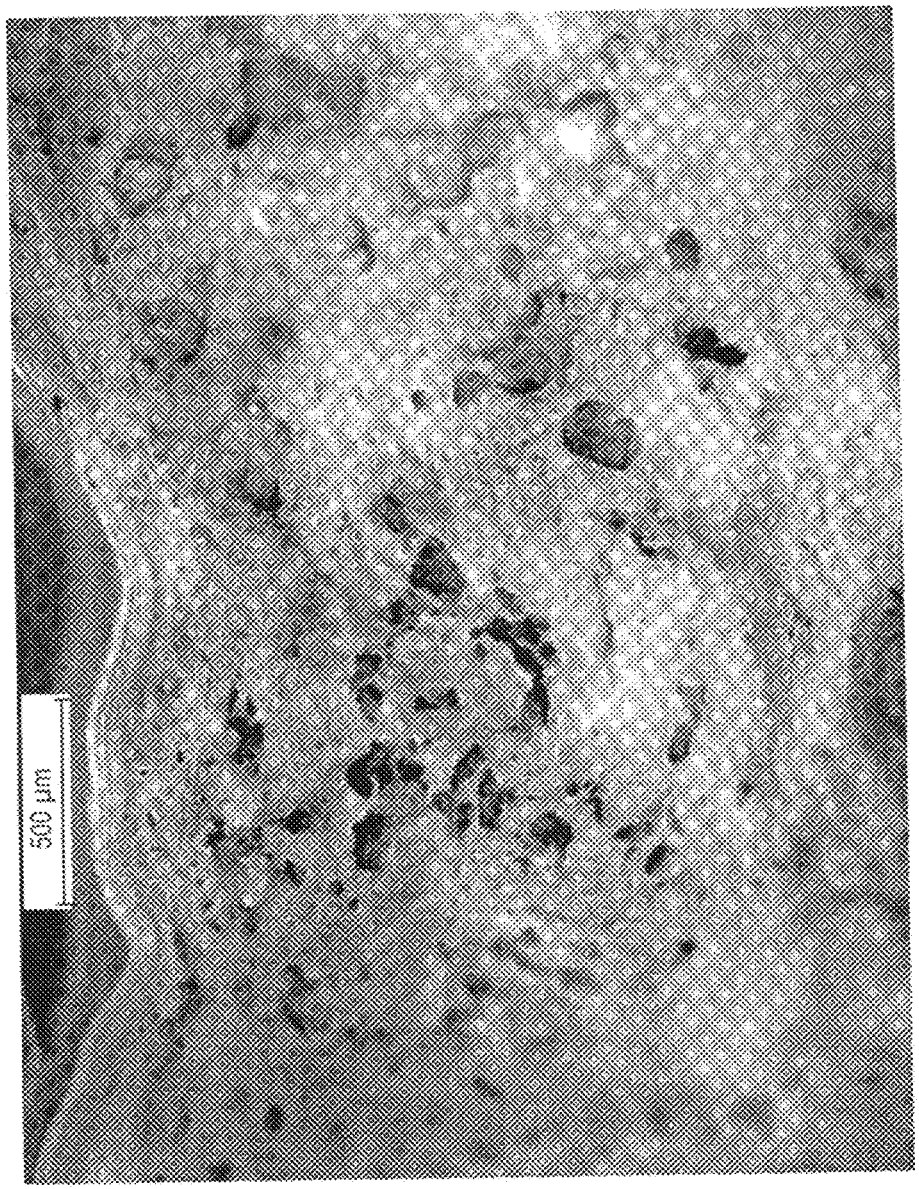

[1] 4.5% Formalin solution, Carl Roth, Karlsruhe, Germany
[2] $H_2O_2$ 3%, Fischar, Saarbrücken, Germany
[3] Monoklonal-mouse-anti-human epithelial antigen, clone BerEp4 M0804, Dako REAL antibody diluting agent S2002, DAKO, Hamburg, Germany
[4] Dako washing buffer S3006, DAKO Hamburg, Germany
[5] Dako REAL EnVision HRP rabbit/mouse K5007, DAKO Hamburg, Germany
[6] Dako REAL substrate buffer, DAB + Chromogen, DAKO Hamburg, Germany
[7] Dako REAL haematoxylin S2020, DAKO Hamburg, Germany The result of this examination is shown in FIG. 2. It is shown that by the extremely fast immunohistological labeling within the context of the method according to the invention it can be reached a highly specific labeling with the monoclonal primary antibodies and their detection with secondary antibodies. This was exemplified with tissue from basal cell carcinomas and the use of monoclonal mouse anti-human epithelial antigen (clone BerEp4) antibodies. By using the highly specific immunolabeling the diagnostic reliability of the method according to the invention can be increased in such a manner that the diagnostic reliability of the unspecific and significantly more time-consuming standard method (HE stained paraffin section) is excelled.

Example 3

Apparatus According to the Invention

Figure 3:
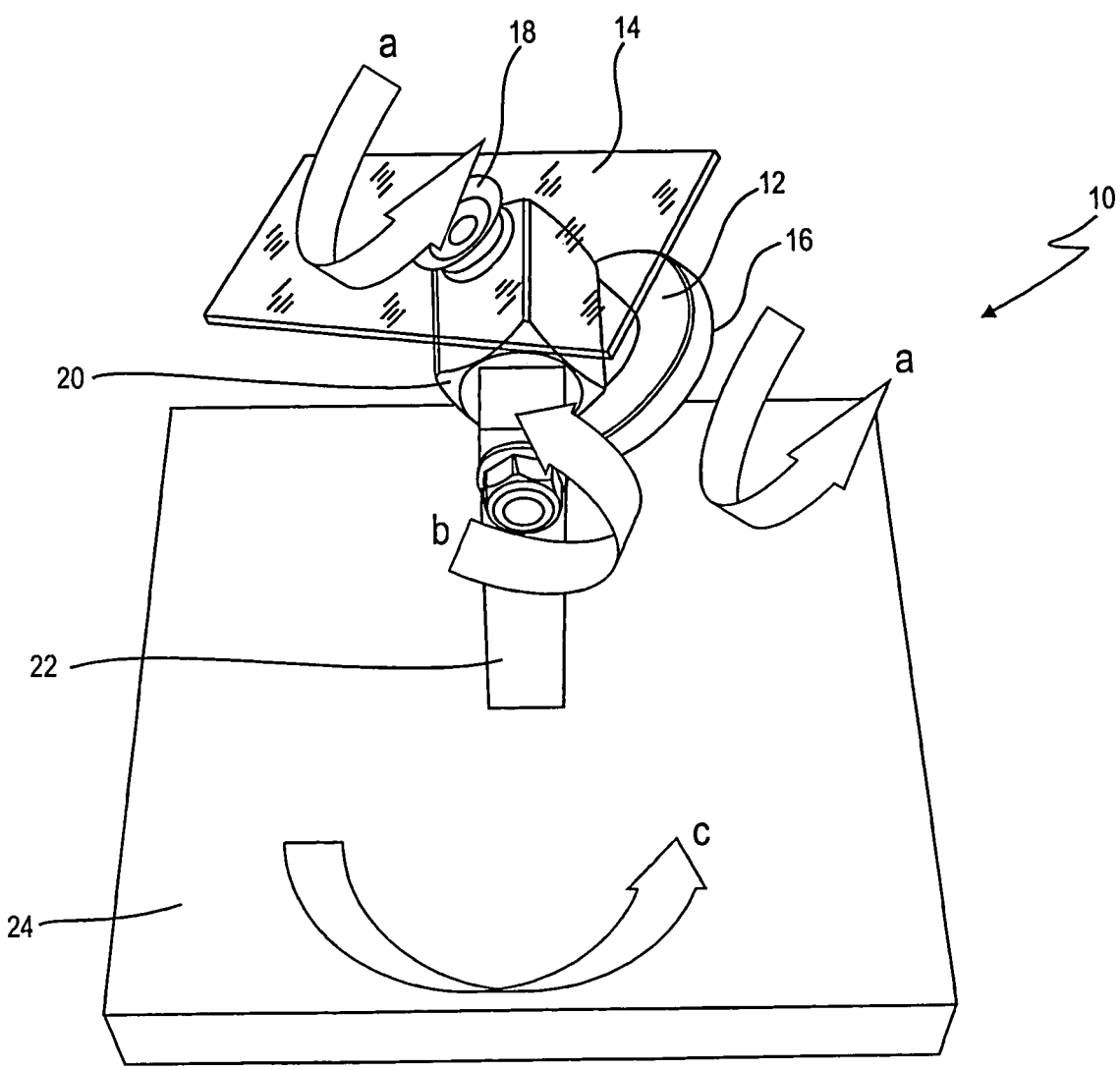
FIG. 3 shows a schematic illustration of an embodiment of the apparatus according to the invention.

In FIG. 3 under the reference number 10 it is shown an example of the apparatus according to the invention for the sterical or three-dimensional orientation of biological material.

The apparatus 10 comprises a receiving element 12 for receiving a carrier 14 for the biological material, e.g. a microscope slide. The receiving element 12 comprises at its first end a rotary knob 16 and at its second end a fastening element 18, e.g. in form of a vacuum cup, which are connected to each other via a first rotary axis. The first rotary axis is rotably supported in a holding element 20 that the receiving element 12 can be rotated by 360° in relation to the holding element 20 by operating the rotary knob 16. This is indicated by the motion arrows a.

The apparatus 10 is further provided with a base element 22. The base element 22 is rotably connected to the holding element 20 via a second axis which is perpendicularly arranged to the first axis of the receiving element 12. Thereby, the receiving element 12 can be rotated with respect to the base element 22 by 360° C., which is indicated by the motion arrow b.

The base element 22 is connected with a foot element 24 for positioning the apparatus on a horizontal plane, e.g. the working or microscopy place. The connection is realized via a third axis which is arranged perpendicularly to the second axis, and via which the base element 22 can be rotated in relation to the foot element 24 by 360°. This is indicated by the motion arrow c. Alternatively, it can be refrained from a rotatability of the base element 22 in relation to the foot element 24. For a three-dimensional inspection of the biological material it is then necessary to rotate the entire apparatus 10 in relation to a horizontal plane; cf. motion arrow c.

The receiving element 12 can be made out of brass, whereas the rotary knob 16 can be made out of plastic. The rotary knob 16 can have a diameter of 30 mm. The vacuum cup 18 is made out of an elastic material which is suited to fasten the carrier 14 for the biological material.

The holding element 20 can be made out of brass and can have the dimensions of 15 mm height, 15 mm width, 25 mm length.

The base element 22 can comprise aluminum and the dimensions of 10 mm width, 10 mm depth, 56 mm height.

The foot element 24 can comprise the dimensions of 100 mm width, 100 mm depth, 12 mm thickness.

By means of the apparatus according to the invention biological material attached to the carrier 14 can be sterically, i.e. three-dimensionally oriented and best visually examined by reflected light microscopy. The biological material usually adheres very good to the surface of the carrier 14 and does not slip off even in a steep position. If necessary, the biological material can be fixed to the carrier 14 by means of a double-sided adhesive tape.

What is claimed is:

1. A method for visual examination of a biological material ex vivo, wherein the biological material is vital biological material which is neither histologically nor optically cut, the method comprising:
   labeling the biological material;
   switching off of reflections at the surface of the biological material; and
   visually examining the biological material by reflected light microscope, without performing a spectrographic analysis of light reflected from the biological material.

2. The method of claim 1, further comprising moisturizing the biological material.

3. The method of claim 2, further comprising fixing the biological material.

4. The method of claim 1, wherein the switching off of reflections at the surface of the biological material comprises use of a transparent medium and a glass carrier, wherein the transparent medium is essentially deposited without inclusion of air or gas between the biological material and the glass carrier and brought into direct contact with the glass carrier.

5. The method of claim 1, wherein the switching off of reflections at the surface of the biological material comprises use of polarized light in the examination by reflected light microscopy.

6. The method of claim 1, wherein labeling the biological material comprises a staining reaction at the biological material.

7. The method of claim 1, wherein labeling the biological material comprises a specific immunoreaction at the biological material.

8. The method of claim 7, wherein the specific immunoreaction comprises:
   contacting the biological material with a primary antibody for binding the primary antibody to the biological material;
   removing the non-bound primary antibody from the biological material; and
   detecting a specific binding of the primary antibody to the biological material.

9. The method of claim 8, wherein detecting a specific binding of the primary antibody to the biological material comprises:
   contacting the biological material with a secondary antibody for binding the secondary antibody to the primary antibody; and
   detecting a specific binding of the secondary antibody to the primary antibody.

10. The method of claim 1, wherein the method is completed within 30 minutes.

* * * * *